United States Patent [19]

Miller

[11] Patent Number: 5,052,418

[45] Date of Patent: Oct. 1, 1991

[54] SOLAR BODY TATTOO

[75] Inventor: David J. Miller, Westmount, Canada

[73] Assignee: Idea Folio Concept Developement Group, Toronto, Canada

[21] Appl. No.: 469,786

[22] Filed: Jan. 24, 1990

[51] Int. Cl.$^5$ ........................................... A45D 40/30
[52] U.S. Cl. .................................... 132/319; 132/333
[58] Field of Search ....................... 132/286, 319, 333; 40/586; 128/743; 101/127

[56] References Cited

U.S. PATENT DOCUMENTS

| | | | |
|---|---|---|---|
| 1,300,592 | 4/1919 | Essig | 132/333 |
| 1,748,403 | 2/1930 | Wentworth | 101/127 |
| 1,854,821 | 4/1932 | Barker | 40/586 |
| 2,033,139 | 3/1936 | Jefferis | 132/319 |
| 2,851,805 | 9/1958 | Allen | 132/319 |

FOREIGN PATENT DOCUMENTS

| | | | |
|---|---|---|---|
| 0333604 | 9/1989 | European Pat. Off. | 132/319 |
| 3420867 | 12/1985 | Fed. Rep. of Germany | 132/319 |
| 0783924 | 7/1935 | France | 132/319 |
| 2425240 | 12/1979 | France | 132/319 |

Primary Examiner—John J. Wilson
Assistant Examiner—Frank A. LaViola
Attorney, Agent, or Firm—Samuel Meerkreebs

[57] ABSTRACT

A tattooing device for producing a temporary predetermined image on the human skin by the action of skin tanning rays comprises a template having a laminated structure which comprises a flexible first layer and a removable second layer. A central opening which is defined in the laminated structure of the template has an outline which corresponds to the image. A first surface of the first layer is provided with an adhesive with the second layer being removably mounted to this first surface. Upon removal of the second layer from the first layer, the latter is applied on the skin at a desired location. A sun block is then distributed on the skin within the central opening. Removal of the first layer from the skin leaves sun block thereon which corresponds to the desired image. Once the skin has been exposed to tanning rays, the sun block is washed away from the skin thereby revealing a skin tattoo. The present invention can also be presented in a kit which includes a series of templates defining central openings having one or more different shapes to produce various images. The kit further includes a sun block such as a colored zinc oxide based cream or lotion. A method for using the present invention is also presented.

1 Claim, 1 Drawing Sheet

SOLAR BODY TATTOO

BACKGROUND OF THE INVENTION

1. Field of the Invention

The present invention relates to non-permanent body images and, more particularly, to a device for producing sun induced body tattoos.

2. Description of the Prior Art

Over the years, various devices and methods for producing non-permanent body tattoos have been developed in order to decorate in multitude of methods, shapes and colours the human skin without resorting to the well known primitive tattooing methods which are painful and result in permanent images on the skin. For instance, images are now produced by the application on the skin of an ink impregnated sponge element having a decorative shape. Other devices include transferable dye images and decal images.

Transferable dye images use water-soluble dyes printed in a certain pattern on a substrate. The image is transferred on the skin by wetting the substrate's pattern and by then pressing the same against the skin. The images so produced are often smeared. Furthermore, perspiration or water coming in contact with the skin will cause the image to streak as the dye is water-soluble. Decal images include a printed image on a substrate which is adhesively positioned on the wearer's skin.

All of the above devices or methods result in images which are either printed on the skin or adhesively mounted thereto.

Conventional permanent tattoos are marked on the skin with a pattern by puncturing the skin and inserting a pigment. From that basic method which uses the skin pigmentation came the concept of producing temporary tattoos on the skin by using the sun's U.V. radiation to selectively, that is with a certain pattern, increase the pigmentation of the skin thereby resulting in the tanning thereof. It is known that U.V. radiation emitted by the sun or by U.V. lamps excites over a period of time the melanocytes in the basal layer of the skin to increase pigmentation. Patented devices using this principle to tattoo the skin are presented hereinbelow.

U.S. Pat. No. 2,851,805, issued on June 26, 1956 to Allen, discloses a mask having a laminated structure and having opaque portions thereof defining a pattern. The mask which is made of a flexible material comprises an adhesive surface whereby the mask can be applied on the body. The mask further includes a central aperture having an outline defining a design provided with an insert layer coloured so as to yield a controlled degree of transparency to skin tanning rays through this central aperture. Submitting the skin provided with such a mask to tanning rays will result in a dark tanned skin around the perimeter of the opaque portion of the mask and in a lighter tanned design on the skin corresponding with central aperture of the mask. The skin positioned under the opaque portion of the mask will remain substantially untanned.

U.S. Pat. No. 1,854,821, issued on Nov. 24, 1932 to Barker, discloses a further mask which comprises cut-out portions forming a predetermined design. The mask can be mounted to a garment such as a bathing suit, whereby exposure of the mask to tanning rays will result in a brown design on the skin corresponding with the cut-out portions of the mask with the skin surrounding the perimeter of the mask being also tanned. Of course, the skin located underneath the uncut portions of the mask will remain substantially untanned.

While the patterns resulting from the ink impregnated sponge element and transferable dye method described briefly hereinbefore produce ink images which are water-soluble and thus inconvenient, the above methods for producing skin tattoos using the tanning rays of the sun are uncomfortable to the wearer as a mask is either adhesively mounted to the wearer's skin or directly mounted to a bathing suit, in which case slight displacement of the mask will result in a relatively blurred pattern on the skin. Furthermore, the swimming suit mounted masks do not offer the possibility of tattooing the skin on every desired part thereof.

SUMMARY OF THE INVENTION

It is therefore an aim of the present invention to provide a device for producing a temporary sun induced skin tattoo.

It is also an aim of the present invention to provide such a device which is of no inconvenience to the wearer.

It is a further aim of the present invention to provide such devices which can be manufactured easily and at low cost in various patterns to produce different images on the skin.

It is a still further aim of the present invention to provide such devices which are aesthetic and comfortable during the tattooing process.

It is a still further aim of the present invention to provide such devices which act as skin moisturizers during the tattooing process.

A construction in accordance with the present invention comprises a tattooing device for producing a temporary predetermined image on the human skin by the action of skin tanning rays. The tattooing device comprises a template means provided with at least one central opening therein which defines an outline corresponding to the image. The template means is provided with adhesion means on a first surface thereof for positioning the template means on the skin in a desired location. This allows a sun block means to be applied at least on the skin within the central opening. Therefore, removal of the template means from the skin leaves the sun block means thereon with the outline of the image. The tanning rays can thus act on the exposed skin.

In a more specific construction in accordance with the present invention, the template means has a laminated structure which comprises a flexible first layer and a removable second layer. The central opening is defined at least in the first layer. A first surface of the first layer is completely provided with the adhesion means thereon. The second layer is removable from the first layer while leaving at least some of the adhesion means on the first surface of the first layer. Therefore, the removable second layer can be peeled from the first layer thus allowing the first layer to be applied on the skin.

Another construction in accordance with the present invention comprises a tattooing kit for producing at least one temporary predetermined image on the human skin by the action of skin tanning rays. The tattooing kit comprises a series of template means each provided with at least one central opening therein defining an outline corresponding to the image. Each of the template means is provided with adhesion means on a first surface thereof for the positioning thereof on the skin in a desired location. The tattooing kit further comprises a sun block means for distribution thereof at least on the skin within the central opening. Therefore, removal of the template means from the skin leaves the sun block means thereon with the outline of the image. The tanning rays can thus act on the exposed skin.

A method in accordance with the present invention for producing a temporary predetermined image on the human skin by the action of skin tanning rays uses a template means having a laminated structure which comprises a flexible first layer and a removable second layer. A central opening is defined at least in the first flexible layer. The central opening defines an outline which corresponds to the image. A first surface of the first layer is provided with adhesion means. The second layer is removably mounted to the first layer and is adapted for, upon removal therefrom, leaving at least some of the adhesion means on the first surface of the first layer. The method comprises the steps of first removing the second layer from the first layer. Second, the first layer is applied on the skin in a desired location with the first surface of the first layer and the adhesion means contacting the skin. Third, a sun block means is applied at least on the skin within the central opening. Fourth, the first layer is removed from the skin thereby leaving thereon the sun block means with the outline of the image. Fifth, the skin adjacent to the sun block means is exposed to the skin tanning rays. Finally, the sun block means is removed from the skin thereby uncovering substantially untanned skin and therefore the image.

BRIEF DESCRIPTION OF THE DRAWINGS

Having thus generally described the nature of the invention, reference will now be made to the accompanying drawings, showing by way of illustration only a preferred embodiment thereof, and in which.

DESCRIPTION OF THE PREFERRED EMBODIMENTS

Figure 1:
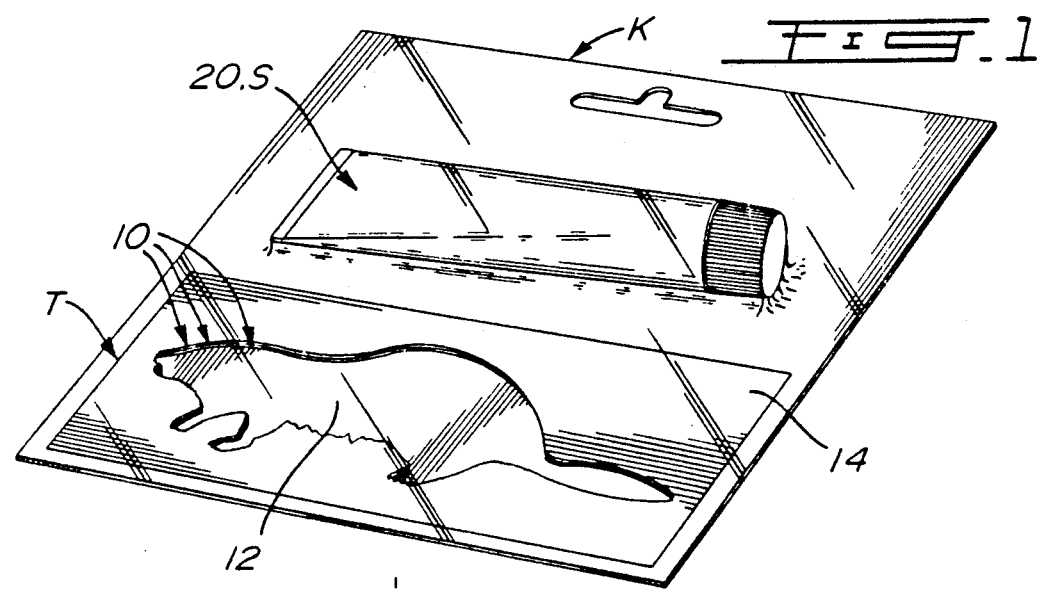
FIG. 1 is a perspective view showing a device presented as a kit in accordance with the present invention for producing a temporary sun induced skin tattoo.

In a preferred construction embodying the present invention, a kit K comprises a series of templates T and a tube 20 containing a sun block cream or lotion S.

Each template 10 of the series of templates T includes in a central portion thereof a cut-out portion 12, the outline of which represents the image that will be sun tattooed on the wearer's skin. In this case, the cut-out central portion 12 represents a beaver.

Each template 10 has a laminated structure including a relatively thin and flexible adhesive layer 14 made of a pressure sensitive, non-irritating, skin compatible, non-toxic and possibly hypoallergenic material. A release paper layer is mounted on the adhesive side of the adhesive layer 14 of the template 10.

The sun block S is a coloured zinc oxide based paste cream or lotion. It can also be a Paba based lotion or cream.

To use the present kit K, a wearer W first peels the release paper from one of the templates 10 and then positions the adhesive layer 14 at a desired location on his or her body, with the adhesive side of the adhesive layer 14 contacting the wearer's skin. Preferably, the adhesive layer 14 is applied to the body without ripples. The flexibility of the adhesive layer 14 allows the wearer to position this adhesive layer 14 on his or her skin with full contact therewith, even on areas of the body which are capricious as to their shape.

Figure 2:
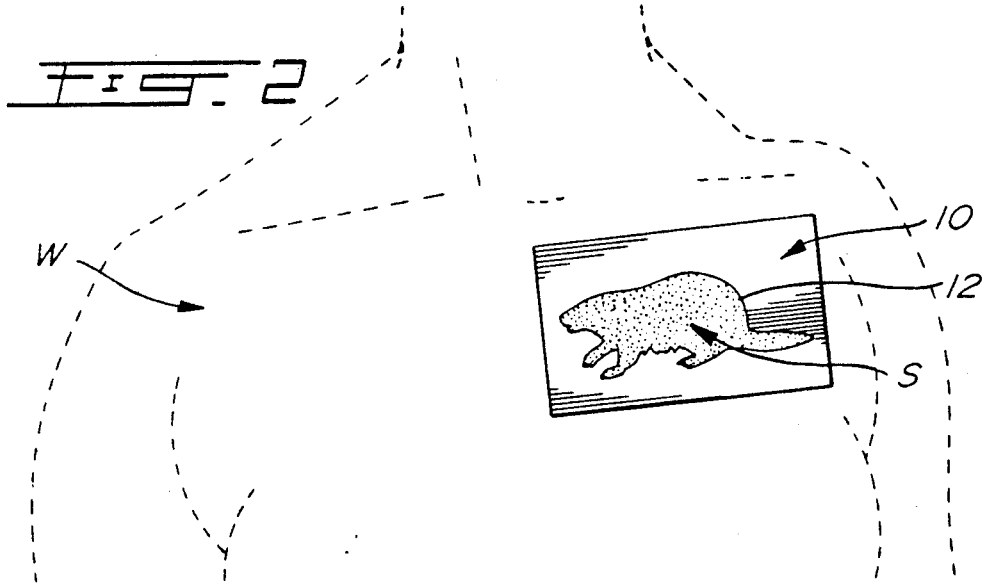
FIG. 2 is a schematic view of the device positioned on the skin of a wearer prior to the skin being submitted to U.V. rays.

The wearer W then uses his or her finger to spread some zinc oxide paste S over the exposed area of the skin within the adhesive layer 14 which corresponds to the central cut-out portion 12 thereof, as seen in FIG. 2. Zinc oxide paste S can also be applied on the uncut portion of the adhesive layer of the template 10. Any desired colour of such a zinc oxide paste S may be used.

Figure 3:
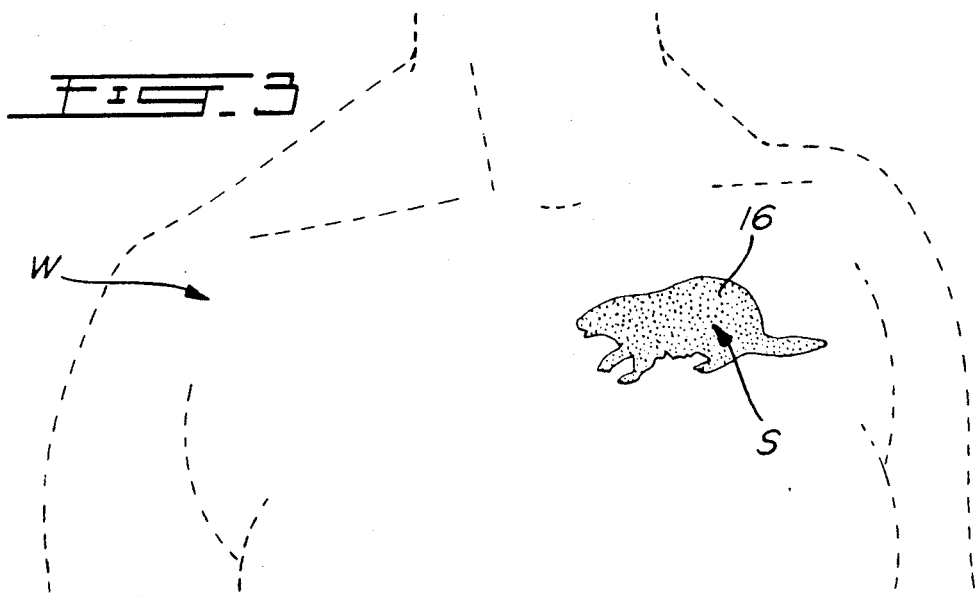
FIG. 3 is a schematic view of a human body equipped with the device of the present invention and ready to be submitted to U.V. rays so as to produce the illustrated beaver image on the skin.

The adhesive layer 14 is then carefully peeled from the wearer's body and then discarded, leaving a beaver-shaped image 16 made of coloured zinc oxide paste S on the wearer's skin, as seen in FIG. 3. The excess of paste S which may have been applied on the uncut portion of the adhesive layer 14 is thus automatically removed thereby providing the image 16 left on the skin with a distinct outline.

As the wearer's skin is exposed to U.V. rays emitted by the sun or by a U.V. lamp, the skin around the beaver-shaped image 16 progressively tans while the skin located therebeneath remains substantially untanned because of the sun blocking qualities of the zinc oxide paste S. It is noted that the zinc oxide paste S acts also as a skin moisturizer. The beaver-shaped zinc oxide image 16 can then be washed away, leaving a beaver image on the wearer's skin. To ensure a clear tattoo, the wearer W must avoid smudging the image 16 during the suntanning process.

From the above, the wearer W first benefits during the suntanning process from an attractive beaver-shaped coloured image 16 on his or her skin. After exposure and once the beaver-shaped image 16 has been removed from the wearer's body, the wearer W benefits from a designer tattoo temporarily defined on his or her skin.

It is easily seen that a multitude of precut templates are possible with different shapes such as corporate logos or popular known shapes such as a man's or a woman's hand, a rose, a kiss, a heart, a dolphin, musical notes, paw prints, foot prints, a happy face, lightening, stripes, a moon crescent, a bow tie, a tie, a champagne bottle, a star, etc.

The sun block S can come in tubes, small jars, pouches, etc. Also, it is not mandatory that the sun block S be included with the templates T in the kit K as the user may purchase independently such a sun block S.

It is further noted that the pressure sensitive adhesive layer 14 of the template 10 leaves no residue on the skin surface after being removed therefrom as the adhesive has greater cohesion to itself and adhesion to the adhesive layer 14 than its adhesion to the skin surface.

The side of the adhesive layer 14 of the template 10 opposite the adhesive side thereof may be made of a glazed paper. The release paper layer is normally glazed for releasing easily from the adhesive side of the adhesive layer 14 and for leaving the adhesive thereon.

I claim:

1. A method for producing a temporary predetermined image on the human skin by the action of skin tanning rays using a template means having a laminated structure comprising a flexible first layer and a removable second layer, a central opening being defined at least in said first flexible layer, said central opening defining an outline corresponding to said image, a first surface of said first layer being provided with adhesion means, said second layer being removably mounted to said first layer and being adapted for, upon removal therefrom, leaving at least some of said adhesion means on said first surface of said first layer, the method comprising the following steps:
 a) removing said second layer from said first layer;
 b) applying said first layer on the skin in a desired location with said first surface of said first layer and said adhesion means left thereon contacting the skin;
 c) choosing a sun block from a group containing zinc oxide paste and Paba based paste;
 d) applying the sun block composition at least on the skin within said central opening;
 e) removing said first layer from the skin thereby leaving thereon at least part of said sun block means which corresponds to said image;
 f) exposing the skin at least adjacent to said sun block means to the skin tanning rays; and
 g) removing the sun block composition from the skin thereby uncovering substantially untanned skin and therefore said image,
whereby only the area previously covered by the sun block composition contrasts with adjacent surfaces which are tanned.

* * * * *